United States Patent [19]
Li et al.

[11] Patent Number: 5,731,449
[45] Date of Patent: Mar. 24, 1998

[54] TRIETHYLENDIAMINE SYNTHESIS WITH BASE-TREATED ZEOLITES AS CATALYSTS

[75] Inventors: Hong-Xin Li; José Guadalupe Santiesteban, both of Allentown; John Nelson Armor, Orefield, all of Pa.

[73] Assignee: Air Products and Chemicals, Inc., Allentown, Pa.

[21] Appl. No.: 716,758

[22] Filed: Sep. 23, 1996

[51] Int. Cl.$^6$ .................................................. C07D 487/18
[52] U.S. Cl. .................................................. 544/352
[58] Field of Search .................................................. 544/352

[56] References Cited

U.S. PATENT DOCUMENTS

| | | | |
|---|---|---|---|
| 3,956,329 | 5/1976 | Murakami et al. | 260/268 |
| 4,703,025 | 10/1987 | Kokotailo et al. | 502/60 |
| 4,804,758 | 2/1989 | Hoelderich et al. | 544/352 |
| 4,966,969 | 10/1990 | Sato et al. | 544/352 |
| 5,041,548 | 8/1991 | Sato et al. | 544/352 |
| 5,243,078 | 9/1993 | Agrawal et al. | 564/470 |

FOREIGN PATENT DOCUMENTS

| | | | |
|---|---|---|---|
| 0158319 | 10/1985 | European Pat. Off. | 544/352 |
| 0312734 | 4/1989 | European Pat. Off. | 544/352 |
| 0313753 | 5/1989 | European Pat. Off. | 544/352 |
| 0382055 | 8/1990 | European Pat. Off. | 544/352 |
| 0423526 | 4/1991 | European Pat. Off. | 544/352 |

OTHER PUBLICATIONS

Liu, Xinshang, Klinowski, Jacek, and Thomas, John M., "Hydrothermal Isomorphous Insertion of Aluminum into the Framework of Zeolite Y:A Convenient Method of Modifying the Siting of Al and Si in Faujastic Catalysts" J. Chem Soc., Chem Commun., 1986 pp.582–584.

Dessau, R.M., Valyocsik, E.W. and Goeke, N. H., "Aluminum Zoning in ZMS–5 as Revealed by Selective Silica Removal" Zeolites, 1992, vol. 12, Sep./Oct. pp. 776–779.

Testova, N.V. Paukshitis, E. A.,and K.G. Ione, "Some Peculiarities in Synthesis of Nitrogen–Containing Heterocyclic Compounds on Zeolite Catalysts", React. Kinet. Caal. Lett., vol. 44, No. 1, 243–249 (1991).

Weitkamp, J. Ernst, S., Buysch, H J., and Lindner, D. "Synthesis of Piperazine and Triethylenediamine Using ZSM–5–Type Zeolite Catalysts", G. Ohlmann, et al. Editors, Catallysis and Adsorption by Zeolites, 1991, Elsevier Science Publishers B. V., Amsterdam, pp. 297–304.

Primary Examiner—Robert T. Bond
Attorney, Agent, or Firm—Michael Leach; William F. Marsh

[57] ABSTRACT

A process for preparing triethylenediamine by passing an ethanolamine, ethyleneamine, piperaziHe or morpholine over a pentasil-type zeolite at elevated temperature characterized by employing a ZSM-5 zeolite in the hydrogen or ammonium form which has been pretreated with an aqueous caustic solution.

14 Claims, No Drawings

TRIETHYLENDIAMINE SYNTHESIS WITH BASE-TREATED ZEOLITES AS CATALYSTS

TECHNICAL FIELD OF THE INVENTION

The present invention relates to the preparation of tdethylenediamine (TEDA) by contacting nitrogen-containing compounds with zeolites at elevated temperature.

BACKGROUND OF THE INVENTION

The synthesis of TEDA from a variety of amine compounds using metallosilicates is well known in the art.

U.S. Pat. No. 3,956,329 discloses a process for preparing TEDA from a number of amine compounds using untreated zeolite catalysts with a $SiO_2/Al_2O_3$ (silica to alumina) ratio between 2 and 12.

U.S. Pat. No. 4,804,758 discloses the preparation of TEDA from certain heterocyclic amines in the presence of borosilicate and/or iron silicate zeolites as catalysts.

U.S. Pat Nos. 4,966,969 and 5,041,548 disclose the preparation of TEDA from amine compounds using a catalyst comprising a crystalline metallosilicate having a silica/metal oxide molar ratio of 12/1 or more, in particular, a metallosilicate crystallized in the presence of an organic crystallizing agent.

EP 158 319 discloses a method of preparing TEDA by contacting acyclic or heterocyclic amines with untreated high-silica zeolite having a silica to alumina ratio of at least 20 to 1.

EP 382 055 discloses a process for synthesizing TEDA from ethylenediamine and 0 to 200 mole % piperazine on aluminum, boron, gallium and/or iron silicate zeolites.

EP 423 526 discloses the preparation of TEDA and piperazine from ethylenediamine-water mixtures which is catalyzed by zeolites of the pentasil type with weakened acidity, i.e., which contain alkali metal ions or in which the aluminum of the zeolite skeleton has been isomorphously replaced by iron.

EP 312 734 discloses that piperazine can be converted directly to TEDA in the presence of zeolites, preferably untreated zeolites having a pentasil, especially a ZSM-5, structure.

EP 313 753 discloses the preparation of mixtures of TEDA and piperazine from polyethylene polyamines and/or ethanolamines using an untreated pentasil zeolite.

The following references disclose caustic treatment of zeolites:

U.S. Pat. No. 4,730,025 discloses a method for purifying zeolitic materials comprising a plurality of solid crystalline phases which uses the variation in solubility between the phase components comprising the materials. Impure zeolite is contacted with a caustic solution under conditions which dissolve at least one of the phases, and the resulting zeolitic material is filtered and washed to produce a purified product. Col 3/23+ states that it is known in the art to expose a zeolite to conditions of high alkalinity to effect a change.

Liu, et al. (*J. Chem. Soc., Chem. Commun.*, 1986, p582) reports the treatment of ultra-stable zeolite Y with an aqueous solution of KOH where non-framework Al was reinserted to the zeolite lattice upon treatment.

Dessau, et al. (*Zeolites*, 1992, vol. 12, p776) shows that treatment of ZSM-5 crystals with an aqueous base solution resulted in partial dissolution of the sample with preferential removal of silica.

SUMMARY OF THE INVENTION

The present invention is directed to a process for preparing TEDA by contacting an amine-containing compound with a pentasil-type zeolite in the hydrogen (H+) and/or ammonium ($NH_4+$) form at elevated temperatures. The zeolite catalyst used in the process is one which has been treated with an aqueous caustic solution prior to its conversion to the H+ or $NH_4+$ form.

Such caustic treatment at least partially deactivates the external sites of the zeolite catalyst for acid catalyzed reactions and surprisingly improves the selectivity toward TEDA production. Some of the amine compounds typically used in making TEDA, such as ethylenediamine (EDA), are very reactive on the external sites of zeolite catalysts giving undesired products.

DETAILED DESCRIPTION OF THE INVENTION

As the starting material to be used in the process for preparing TEDA, any amine compounds having, in the molecule, a moiety represented by the following general formula can be used:

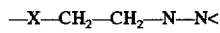

where X is oxygen or nitrogen. Typical examples of suitable amine compounds are ethanolamines, including monoethanolamine, diethanolamine and tdethanolamine; ethyleneamines, including ethylenediamine, diethylenetdamine and triethylene-tetramine; piperazine and its derivatives N-hydroxyethylpiperazine and N-aminoethylpiperazine; morpholine and obviously mixtures of the foregoing.

The crystalline metallosilicate (zeolite), which is used as the catalyst in the process, has a crystal skeleton mainly comprised of silicon dioxide, (silica; $SiO_2$) and aluminum oxide (alumina; $Al_2O_3$), iron oxide or boron oxide. Alumina is the preferred metal oxide. The silica/metal oxide molar ratio is 12:1 or more, preferably 25:1 to 1000:1, and more preferably 50:1 to 500:1. If the silica/metal oxide molar ratio is less than 12:1, the yield Of TEDA is undesirably low.

There are no special limitations to the crystalline aluminosilicate that is used as long as it satisfies the above silica/alumina molar ratio. Crystalline aluminosilicates having a main pore made of a ten-membered ring of oxygen, especially those belonging to members of the pentasil-type structure, are preferred with ZSM-5 zeolite being most preferred.

The preparation of suitable pentasil zeolite catalysts is well known to those skilled in the art as illustrated by the previously cited patents and literature references. In addition, suitable pentasil zeolites are commercially available from many sources such as Degussa AG and CU Chemie Uetikon AG.

Crystalline aluminosilicates of the pentasil family as obtained by the hydrothermal synthesis using an organic crystallizing agent are particularly preferred. Among the pentasil types, the zeolite structures ZSM-5, ZSM-11, ZSM-8, and ZSM-5/ZSM-11-intermediates are preferred, especially ZSM-5.

The zeolite catalysts are used in their hydrogen form (H+) and/or their ammonium form ($NH_4+$) after having undergone the aqueous caustic solution pretreatment.

For example, a pentasil-type crystalline aluminosilicate can be prepared by the hydrothermal synthesis using a mixture composed mainly of a silica source, e.g., colloidal silica, silica gel, or silicic acid salts such as water glass, and an aluminum oxide source, e.g., the sulfuric acid salts, nitric acid salts or oxy acid salts of alumina, such as aluminum sulfate and sodium aluminate, in the absence or preferably in the presence of an organic crystallizing agent, e.g., amines such as tetraalkylammonium halide having 2 to 5 carbon atoms.

There is also known a method in which the hydrothermal synthesis is performed in the presence of alkali metal compounds such as the hydroxides and halides of alkali metal such as sodium and the like.

The crystalline aluminosilicate obtained by these methods is generally not of the H+ or $NH_4+$ form, but of the form that H+ and $NH_4+$ are replaced by quaternary ammonium ion and/or alkali metal ion such as Na+ and the like. Therefore, the crystalline aluminosilicate must be changed into the H+ or $NH_4+$ form, and this exchange can be easily achieved by known methods after the aqueous caustic solution treatment.

With regard to the caustic treatment, the prepared aluminosilicate is contacted, for example, with an aqueous 0.1 to 5 molar caustic solution, such as sodium or potassium hydroxide or even ammonium hydroxide, at 0° to 100° C. for 0.01 to 100 hours, preferably 0.5 to 3 molar caustic solution at 20° to 80° C. for 0.5 to 5 hours. It is desirable to perform such contact using 10 to 30 ml aqueous solution/g zeolite.

For changing the alkali metal ion of the caustic treated zeolite into H+ or $NH_4+$, there is often employed a method in which the alkali metal salt-type crystalline aluminosilicate is treated with an aqueous solution of ammonium salts, such as ammonium nitrate and ammonium sulfate, to form an ammonium salt-type crystalline aluminosilicate. The ammonium salt-type crystalline aluminosilicate may then be calcined in the air at a temperature of 300° to 600° C., preferably 400° to 500° C., to obtain the H+ form crystalline zeolite.

While the zeolite as used in the present invention is preferably of the H+ and/or $NH_4+$ form, the H+ and/or $NH_4+$ may be partially replaced by other cations, such as alkali, alkaline earth, rare earth, transition metals, oxides etc., as long as the object of the present invention can be obtained.

The catalyst of the present invention can be used in any desired form, such as powder, particles, strips, spheres and pellets. The catalyst can be self-bound or molded with a binder such as silica, alumina, titania, zirconia, natural clays and/or mixtures of these materials be mixed with the zeolite. Naturally occurring clays which can be composited with the zeolite catalyst include the montmorillonite and kaolin family. These clays can be used in the raw state as originally mined or initially subjected to calcination, acid treatment or chemical modification.

Of all the matrix materials mentioned above, materials of low acidity such as silica or zirconia are preferred in that they prevent unwanted side reactions engendered by more active materials such as alumina. The performance of alumina can, however, be improved by altering its acid properties via chemical modification.

The relative proportions of zeolite and matrix material can vary widely with the zeolite content ranging from 10 to 98 wt %, and more usually in the range of 50 to 90 wt %, of the composite.

In accordance with the process of the present invention, the desired TEDA can be efficiently obtained by reacting amine compounds having in the molecule a group represented by the general formula:

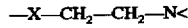

as the starting material using the described zeolite catalyst under pressures ranging from 0.001 to 200 atm (0.1 to 20,000 kPa), preferably 0.01 to 10 atm (1 to 1000 kPa).

The reaction of the amine compound proceeds on contacting it with the described zeolite catalyst under the above-specified pressure. Reaction conditions, such as reaction temperature, reaction time and starting materials/catalyst ratio, cannot be determined unconditionally because they vary with the type of amine compound, the type of zeolite catalyst, reaction pressure and the like. Usually the reaction temperature is chosen within the range 100° to 450° C., preferably 300° to 400° C.

The reaction can be performed batch-wise, semi-continuously or continuously. In the case of the continuous reaction, WHSV (weight hourly space velocity) is not critical, but usually ranges from 0.01 to 10 $hr^{-1}$. The preferred WHSV is determined depending on the temperature. For example, at 300° C., WHSV is 0.02 to 2 $hr^{-1}$, and at 350° C., it is 0.1 to 5 $hr^{-1}$.

In the reaction of the amine compound as a starting material, it may be diluted with an inert gas such as hydrogen, nitrogen, steam or hydrocarbons, or with an inert solvent such as water and inert hydrocarbons. By using these diluents, the reaction can be controlled appropriately.

EXAMPLE 1

Preparation of HZSM-5

A 40 g NaZSM-5 sample (obtained from Degussa AG Modul 180) was exchanged with 800 mL of 1.0M aqueous $NH_4NO_3$ solution. The solid was filtered, washed with deionized water, and dried at 110° C. to yield $NH_4$_ZSM-5. HZSM-5 was obtained by calcination of the $NH_4$_ZSM-5 at 500° C. Chemical analysis showed that the HZSM-5 had a silica/alumina molar ratio of 160 and contained less than 0.01 wt % Na.

EXAMPLE 2

Preparation of Base-treated HZSM-5

A 10 g NaZSM-5 sample (obtained from Degussa AG, Modul 180) was stirred in 250 mL of 2.0M NaOH solution at room temperature for two hours. The solid was filtered, washed with deionized water and dried at 110° C. The base-treated sample was then exchanged with 200 mL of 1.0M aqueous $NH_4NO_3$ solution to obtain $NH_4$_ZSM-5. HZSM-5 was obtained by calcination of the $NH_4$_ZSM-5 at 500° C. Chemical analysis showed that the HZSM-5 had a silica/alumina molar ratio of 153 and contained less than 0.01 wt % Na.

The catalysts of Examples 1 and 2 were characterized by infrared spectroscopy. Excess hydroxyl groups (broad band centered at 3458 $cm^{-1}$ in the spectrum) were present in the non-treated HZSM-5 material. These excess hydroxyl groups were successfully removed after base treatment as was evidenced by infrared spectroscopy.

EXAMPLES 3 AND 4

TEDA Synthesis

Reactions were carried out in a plug-flow reactor at atmospheric pressure. Typically, 1 cc (about 0.6 g) of catalyst particles of 18–35 mesh were loaded into the reactor. The reactor was heated to 340° C. under a flow of nitrogen. Aqueous ethylenediamine (EDA) solution (25 wt %) was fed to the reactor with a syringe pump at 0.6 mL/hr. Nitrogen gas was co-fed to the reactor at 8 mL/min. Example 3 used the unmodified HZSM-5 catalyst from Example 1 while Example 4 used the HZSM-5 catalyst treated with sodium hydroxide from Example 2. The results in Table 1 show that base treatment not only increased the TEDA yield on the HZSM-5 catalyst, but also prevented catalyst deactivation as was observed for nontreated HZSM-5.

TABLE 1

|  | Catalyst NaOH Treatment | Time on Stream (hr) | EDA Conversion (%) | TEDA Molar Selectivity (%) |
|---|---|---|---|---|
| Example 3 | No | 6 | 96.0 | 21.0 |
|  |  | 21 | 88.7 | 22.9 |
| Example 4 | Yes | 6 | 100 | 56.3 |
|  |  | 32 | 100 | 54.5 |

INDUSTRIAL APPLICATION

The present invention provides an improvement in the production of TEDA from amine compounds using a zeolite catalyst.

We claim:

1. In a process for preparing triethylenediamine by passing an amine compound over a pentasil-type zeolite at elevated temperature, the improvement which comprises employing a pentasil-type zeolite in the hydrogen or ammonium form which has been pretreated with an aqueous caustic solution.

2. The process of claim 1 in which the caustic is sodium or potassium hydroxide.

3. The process of claim 2 which uses a 0.1 to 5 molar aqueous caustic solution.

4. The process of claim 3 which uses 10 to 30 mL aqueous caustic solution/g zeolite.

5. The process of claim 3 in which the zeolite has a silica/metal oxide molar ratio of 25:1 to 1000:1.

6. The process of claim 5 in which the zeolite is a ZSM-5, ZSM-8 or ZSM-11 zeolite.

7. The process of claim 1 in which the amine compound has, in the molecule, a moiety represented by the following general formula $$-X-CH_2-CH_2-N<$$

where X is oxygen or nitrogen.

8. In a process for preparing triethylenediamine by passing an amine compound having, in the molecule, a moiety represented by the following general formula $$-X-CH_2-CH_2-N<$$

where X is oxygen or nitrogen, over a pentasil-type zeolite at elevated temperature, the improvement which comprises employing a ZSM-5 zeolite in the hydrogen or ammonium form which has been pretreated with a 0.1 to 5 molar aqueous sodium or potassium hydroxide solution.

9. The process of claim 8 in which the amine compound is an ethanolamine, an ethyleneamine, a piperazine or morpholine.

10. The process of claim 8 in which the amine compound is ethylenediamine.

11. The process of claim 3 which uses 10 to 30 mL aqueous caustic solution/g zeolite.

12. The process of claim 8 in which the zeolite has a silica/alumina molar ratio of 25:1 to 1000:1.

13. In a process for preparing triethylenediamine by passing an ethanolamine, an ethyleneamine, a piperazine or morpholine over a pentasil-type zeolite at elevated temperature, the improvement which comprises employing a ZSM-5 zeolite having a silica/alumina molar ratio of 25:1 to 1000:1 in the hydrogen or ammonium form which has been pretreated with a 0.1 to 5 molar aqueous caustic solution.

14. The process of claim 13 in which the zeolite has a silica/alumina molar ratio of 50:1 to 500:1.

* * * * *